(12) United States Patent
Shitara et al.

(10) Patent No.: US 8,491,902 B2
(45) Date of Patent: Jul. 23, 2013

(54) MEDICAMENT COMPRISING RECOMBINANT ANTIBODY AGAINST CHEMOKINE RECEPTOR CCR4

(75) Inventors: Kenya Shitara, Fujisawa (JP); Rinpei Niwa, Machida (JP); So Ohta, Machida (JP); Yuka Sasaki, Machida (JP); Junji Kanazawa, Ube (JP); Toshihiko Ishii, Sunto-gun (JP); Shiro Akinaga, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 202 days.

(21) Appl. No.: 10/581,413

(22) PCT Filed: Dec. 3, 2004

(86) PCT No.: PCT/JP2004/018430
§ 371 (c)(1),
(2), (4) Date: Jun. 23, 2006

(87) PCT Pub. No.: WO2005/053741
PCT Pub. Date: Jun. 16, 2005

(65) Prior Publication Data
US 2007/0020263 A1   Jan. 25, 2007

(30) Foreign Application Priority Data

Dec. 4, 2003 (JP) ................... 2003-406590
May 25, 2004 (JP) ................... 2004-155141

(51) Int. Cl.
*A61K 39/395* (2006.01)
(52) U.S. Cl.
USPC ................... 424/142.1; 424/141.1; 424/130.1
(58) Field of Classification Search
None
See application file for complete search history.

(56) References Cited

U.S. PATENT DOCUMENTS

| | | | |
|---|---|---|---|
| 6,488,930 B1 * | 12/2002 | Wu et al. | 424/143.1 |
| 6,762,174 B1 * | 7/2004 | Taub | 514/90 |
| 7,138,117 B1 | 11/2006 | Wu et al. | |
| 2002/0098527 A1 | 7/2002 | Shitara et al. | |
| 2003/0175273 A1 * | 9/2003 | Shitara et al. | 424/144.1 |

FOREIGN PATENT DOCUMENTS

| | | |
|---|---|---|
| JP | 2002-539079 | 11/2002 |
| JP | 2002-544173 | 12/2002 |
| WO | 00/42074 A1 | 7/2000 |
| WO | WO 00/67795 | 11/2000 |
| WO | WO 01/64754 | 9/2001 |
| WO | WO 02/12347 | 2/2002 |
| WO | WO 021010743 | 2/2002 |
| WO | WO 03/018635 | 3/2003 |

OTHER PUBLICATIONS

Rudikoff et al. PNAS 1982 vol. 79, pp. 1979-1983.*
Rader et al. PNAS. 1998. 95:8910-8915.*
The Merck Manuals Online Medical Library, [online]. Whitehouse Station, NJ: Merck Research Laboratories, 2006-2007. [retrieved on Oct. 10, 2007]. Retrieved from the Internet: < URL: http://www.merck.com/mmpe/print/sec11/ch143/ch143b.html >. Hodgkin lymphoma, pp. 1-5.*
The Merck Manuals Online Medical Library, [online]. Whitehouse Station, NJ: Merck Research Laboratories, 2006-2007. [retrieved on Oct. 10, 2007]. Retrieved from the Internet: < http://www.merck.com/mmpe/print/sec11/ch142/ch142a.html >. Leukemia, see pp. 1-4.*
Padlan et al. PNAS 1989, 86:5938-5942.*
Bendig Methods: A Companion to Methods in Enzymology 1995; 8:83-93.*
Goldenberg, "Trastuzumab, a Recombinant DNA-Derived Humanized Monoclonal Antibody, a Novel Agent for the Treatment of Metastatic Breast Cancer", Clinical Therapeutics, vol. 21, No. 2 (1999), pp. 309-317.
Czuczman, et al, "Treatment of Patients With Low-Grade B-Cell Lymphoma With the Combinatino of Chimeric Anti-CD20 Monoclonal Antibody and CHOP Chemotherapy", Journal of Clinical Oncology, vol. 17, No. 1 (1999), pp. 268-276.
Friedberg, et al, "Combination Immunotherapy with Rituximab and Interleukin 2 in Patients with Relapsed or Refractory Follicular Non-Hodgkin's Lymphoma", British Journal of Hematology, vol. 117 (2002), pp. 828-834.
Van Der Kolk, Le, et al., "Treatment of Relapsed B-Cell non-Hodgkin's Lymphoma With a Combinatino of Chimeric Anti-CD20 Monoclonal Antibodies (rituximab) and G-CSF: Final Report on Safety and Efficacy", Leukemia, vol. 17 (2003), pp. 1658-1664.
Takeuchi, "Chemical Therapy for Adult ALL", Igaku no Ayumi (Progress Med. Sci.), vol. 190, No. 5 (1999), pp. 474-480.
Ohnishi, "Standard Theraphy of CML", Igaku no Ayumi (Progress Med. Sci.), vol. 190, No. 5 (1999), pp. 481-485.
Kusumoto, "Usage of cytokine at therapy of acute leukemia", Igaku no Ayumi (Progress Med. Sci.), vol. 190, No. 5 (1999), pp. 522-529.
Supplemental European Search Report issued Feb. 20, 2008 in EP 04801651.3-1222.
Dimitri Flieger et al., "Enhancement of Antibody Dependent Cellular Cytotoxicity (ADCC) by Combination of Cytokines", Hybridoma, 1999, 18(1):63-68.
Examiner's Report for Australian Patent Application No. 2004294842, dated Aug. 17, 2009.

* cited by examiner

*Primary Examiner* — Sharon Wen
(74) *Attorney, Agent, or Firm* — Sughrue Mion, PLLC

(57) ABSTRACT

A medicament having a higher therapeutic effect than that provided by administration of a recombinant antibody against human CC chemokine receptor 4 or an antibody fragment thereof or an agent alone is provided.

17 Claims, 6 Drawing Sheets

MEDICAMENT COMPRISING RECOMBINANT ANTIBODY AGAINST CHEMOKINE RECEPTOR CCR4

This is a National Stage entry of Application No. PCT/JP2004/018430, filed Dec. 3, 2004; the disclosure of which is incorporated herein by reference in its entirety.

TECHNICAL FIELD

The present invention relates to a medicament comprising a combination of a recombinant antibody which specifically binds to human CC chemokine receptor 4 (CCR4) or an antibody fragment thereof and at least one agent.

BACKGROUND ART

When a ligand is bound to a chemokine receptor, migration of leukocytes is induced. Human CC chemokine receptor 4 (hereinafter referred to as CCR4) which is mainly expressed on a Th2-type CD4-positive helper T cell in a normal tissue is one type of a chemokine receptor family [Int. Immunol., 11, 81 (1999)]. CCR4 binds specifically to TARC (thymus and activation-regulated chemokine) or MDC (macrophage-derived chemokine). The Th2-type CD4-positive helper T cell which controls humoral immunity is considered to play an important role in allergic diseases or autoimmune diseases.

In T cell-type leukemia/lymphoma cells described above, various chemokine receptors are expressed, and there is a relation between subtypes of T cell leukemia/lymphoma and types of receptors expressed in cells. It was reported that CCR4 is expressed at high frequency in leukemia/lymphoma cells [Blood, 96, 685 (2000)]. Since CCR4 is expressed at high frequency in ALK-positive anaplastic large-cell lymphoma and mycosis fungoides, a possibility of CCR4 being a tumor marker having quite a high selectivity in specific carcinomas was suggested [Blood, 96, 685 (2000), Mod. Pathol., 15, 838 (2002), J. Invest. Dermatol., 119, 1405 (2002)]. It was reported that CCR4 is expressed at quite a high frequency also in adult T-cell leukemia (hereinafter referred to as ATL) caused by infection with human T-cell leukemiavirus type I) [Blood, 99, 1505 (2002)]. Regarding the expression of CCR4 in ATL, the expression of CCR4 significantly correlates with bad prognosis [Clin. Cancer Res., 9, 3625 (2003)]. Further, CCR4 is selectively expressed in cells of cutaneous T cell lymphoma (hereinafter referred to as CTL) [J. Invest. Dermatol., 119, 1405 (2002)].

Method for treating leukemia/lymphoma is mainly chemotherapy using a combination of plural low-molecular anticancer agents. However, chemotherapy that provides satisfactory therapeutic effects has been so far unknown [Gan to Kagaku Ryoho, 26, Supplement I, 165-172 (1999)].

Among the CCR4-positive leukemia/lymphoma described above, prognosis of ATL is poor in particular. Concerning patients who suffer from acute or lymphatic leukemia occupying more than 70% of total ATL and have experienced common CHOP therapy (therapy using cyclophosphamide, vincristine, doxorubicin and prednisone in combination), 4-year survival rate is approximately 5% [British J. Haematol., 79, 428-437 (1991)].

In usual chemotherapy, it is sometimes difficult to induce remission because of advent of drug-resistant tumor cells or the like. However, excellent therapeutic results are sometimes obtained by combination of chemotherapy and an antibody. Anti-HER2/neu humanized antibody rhuMAb HER2 (Herceptin/trastuzumab, Roche) exhibited an outstanding effect against breast cancer in combination therapy with a taxane anticancer agent [Clinical Therapeutics, 21, 309 (1999)]. Anti-CD20 human chimeric antibody IDEC-C2B8 (Rituxan/rituximab, IDEC) exhibited an outstanding effect against B cell lymphoma by combination therapy with multiple drug therapy [J. Clin. Oncol., 17, 268 (1999)].

Combination therapy using an antibody and a cytokine is also expected as new immunotherapy against tumors. A cytokine is a general term for various humoral factors that control intracellular interaction in an immune reaction. An antibody-dependent cell-mediated cytotoxic activity (hereinafter referred to as ADCC), one of cytotoxic activities, is induced by binding an antibody to an effector cell such as a mononuclear cell, a macrophage or an NK cell [J. Immunol., 138, 1992 (1987)]. For the purpose of activating an effector cell, combination therapy using a combination of an antibody and a cytokine has been attempted. With respect to B cell leukemia/lymphoma, a clinical test administrating IDEC-C2B8 and interleukin (IL)-2 [British J. Haematol., 117, 828-834 (2002)] or IDEC-C2B8 and granulocyte-colony stimulating factor [Leukemia, 17, 1658-1664 (2003)] in combination has been conducted. However, an outstanding therapeutic effect has not been observed in comparison with use of the antibody alone.

Anti-CCR4 antibody KM2760 has been known as a therapeutic agent against the CCR4-positive leukemia/lymphoma that selectively reduces tumor cells via ADCC (WO 03/18635). Combined use of an anti-CCR4 antibody and a chemotherapeutic agent or a cytokine has been unknown so far.

In treatment of cancers, especially, leukemia and lymphoma, a therapeutic method that brings forth satisfactory effects has been unknown so far.

DISCLOSURE OF THE INVENTION

The object of the present invention is to provide a medicament comprising a combination of anti-CCR4 recombinant antibody or an antibody fragment thereof and at least one agent.

The present invention relates to the following (1) to (26).

(1) A medicament comprising a combination of a recombinant antibody which specifically binds to human CC chemokine receptor 4 (CCR4) or an antibody fragment thereof and at least one agent.

(2) A medicament for administering a combination of a recombinant antibody which specifically binds to CCR4 or an antibody fragment thereof and at least one agent.

(3) A medicament for administering a recombinant antibody which specifically binds to CCR4 or an antibody fragment thereof and at least one agent either simultaneously or successively.

(4) The medicament according to any one of the above (1) to (3), which is an antitumor drug.

(5) The medicament according to the above (4), wherein the tumor is a tumor in which CCR4 is expressed.

(6) The medicament according to the above (5), wherein the tumor in which CCR4 is expressed is a hematopoietic organ tumor.

(7) The medicament according to any one of the above (1) to (6), wherein the recombinant antibody which specifically binds to CCR4 or the antibody fragment thereof is an antibody which specifically binds to an extracellular region of CCR4 and does not show a reactivity to a human platelet.

(8) The medicament according to the above (7), wherein the recombinant antibody which specifically binds to the extracellular region of CCR4 or the antibody fragment thereof does not have an activity of inhibiting binding of TARC (thymus and activation-regulated chemokine) or MDC (macrophage-derived chemokine) as a CCR4 ligand to CCR4.

(9) The medicament according to the above (7) or (8), wherein the extracellular region is an extracellular region selected from the group consisting of 1 to 39, 98 to 112, 176 to 206 and 271 to 284 of an amino acid sequence represented by SEQ ID No. 1.

(10) The medicament according to any one of the above (7) to (9), wherein the extracellular region is an epitope existing at positions 2 to 29 of the amino acid sequence represented by SEQ ID No. 1.

(11) The medicament according to any one of the above (7) to (10), wherein the extracellular region is an epitope existing at positions 13 to 29 of the amino acid sequence represented by SEQ ID No. 1.

(12) The medicament according to any one of the above (7) to (11), wherein the extracellular region is an epitope existing at positions 13 to 25 of the amino acid sequence represented by SEQ ID No. 1.

(13) The medicament according to the above (12), wherein in the recombinant antibody which specifically binds to CCR4 or the antibody fragment thereof, a binding activity to a peptide comprising 13 to 25 of the amino acid sequence represented by SEQ ID No. 1 in which at least one of tyrosine residues 16, 19, 20 and 22 is sulfated is lower than a binding activity to a peptide comprising 13 to 25 of the amino acid sequence represented by SEQ ID No. 1.

(14) The medicament according to any one of the above (1) to (13), wherein the recombinant antibody which specifically binds to the extracellular region of CCR4 or the antibody fragment thereof is an antibody which specifically reacts with an epitope recognized by a monoclonal antibody which hybridoma KM2160 (FERMBP-10090) produces or an antibody fragment thereof.

(15) The medicament according to any one of the above (1) to (14), wherein the human recombinant antibody is a human chimeric antibody or a human CDR-grafted antibody.

(16) The medicament according to the above (15), wherein the human chimeric antibody comprises complementarity determining regions (CDRs) of a heavy chain (H chain) variable region (V region) and a light chain (L chain) V region of a monoclonal antibody which specifically binds to CCR4.

(17) The medicament according to the above (15) or (16), wherein the human chimeric antibody comprises CDR1, CDR2 and CDR3 of a heavy chain (H chain) variable region (V region) of an antibody comprising amino acid sequences represented by SEQ ID Nos. 5, 6 and 7, respectively and/or CDR1, CDR2 and CDR3 of a light chain (L chain) variable region (V region) of an antibody comprising amino acid sequences represented by SEQ ID Nos. 8, 9 and 10, respectively.

(18) The medicament according to the above (15) to (17), wherein the human chimeric antibody comprises a heavy chain (H chain) variable, region (V region) of an antibody molecule comprising an amino acid sequence represented by SEQ ID No. 11 and/or a light chain (L chain) V region of an antibody molecule represented by SEQ ID No. 12.

(19) The medicament according to the above (15), wherein the human CDR-grafted antibody comprises complementarity determining regions (CDRS) of a heavy chain (H chain) variable region (V region) and a light chain (L chain) V region of a monoclonal antibody which specifically binds to CCR4.

(20) The medicament according to the above (15) or (19), wherein the human CDR-grafted antibody comprises CDR1, CDR2 and CDR3 of a heavy chain (H chain) variable region (V region) of an antibody comprising amino acid sequences represented by SEQ. ID Nos. 5, 6 and 7, respectively and/or CDR1, CDR2 and CDR3 of a light chain (L chain) V region comprising amino acid sequences represented by SEQ ID Nos. 8, 9 and 10, respectively.

(21) The medicament according to any one of the above (15), (18) and (20), wherein the human CDR-grafted antibody comprises a heavy chain (H chain) variable region (V region) of an antibody molecule comprising an amino acid sequence represented by SEQ ID No. 16 or 17 and/or a light chain (L chain) V region of an antibody molecule represented by SEQ ID No. 18.

(22) The medicament according to any one of the above (1) to (21), wherein the agent is a protein or an agent having low-molecular weight.

(23) The medicament according to the above (22), wherein the protein is a cytokine or an antibody.

(24) The medicament according to the above (23), wherein the cytokine is a cytokine selected from G-CSF, M-CSF, interferon-α, IL-2 and IL-15.

(25) The medicament according to any one of the above (1) to (24), wherein the agent having low-molecular weight is a chemotherapeutic agent or a hormone therapeutic agent.

(26) The medicament according to the above (25), wherein the chemotherapeutic agent is an agent selected from vincristine, cyclophosphamide, etoposide and Methotrexate.

Examples of the medicament in the invention include a medicament comprising a combination of the recombinant antibody which specifically reacts with CCR4 or the antibody fragment thereof and at least one agent, a medicament for administering the recombinant antibody which specifically reacts with CCR4 or the antibody fragment thereof and at least one agent in combination, and a medicament for administering the recombinant antibody which specifically reacts with CCR4 or the antibody fragment thereof and at least one agent either simultaneously or successively.

The medicament comprising a combination refers to a medicament in which the recombinant antibody which specifically binds to CCR4 or the antibody fragment thereof and at least one agent are prepared separately and these are administered in combination either simultaneously or successively or a mixed medicament obtained by mixing each ingredient. The mixed medicament obtained by mixing each ingredient includes a fusion antibody obtained by binding at least one agent to the recombinant antibody which specifically binds to CCR4 or the antibody fragment thereof, and the like.

The recombinant antibody which specifically binds to CCR4 and the antibody fragment thereof in the invention (both of which are sometimes referred to as an antibody of the invention) include a recombinant antibody which specifically reacts with an extracellular region of human CCR4 and an antibody fragment thereof. A recombinant antibody which does not show a reactivity to a human platelet or an antibody fragment thereof, a recombinant antibody having high ADCC or an antibody fragment thereof, and the like are preferable.

That an antibody does not show a reactivity to a human platelet as here referred to means that an antibody does not substantially reactive with a human platelet. Specifically, it means that a reactivity is not shown by the measurement with a flow cytometer.

Further, the antibody of the present invention include an antibody which specifically reacts with the region comprising positions 1 to 39, 98 to 112, 176 to 206 or 271 to 284 in the amino acid sequence represented by SEQ ID NO:1; an antibody which specifically reacts with positions 2 to 29 (SEQ ID NO:2) in the amino acid sequence represented by SEQ ID NO: 1 is preferred, an antibody which specifically reacts with and positions 12 to 29 (SEQ ID NO:3) in the amino acid sequence represented by SEQ ID NO: 1 is more preferred and an antibody which specifically reacts with positions 13 to 25 (SEQ ID NO:4) in the amino acid sequence represented by SEQ ID NO:1 is most preferred. The antibody also includes an antibody which specifically reacts with an epitope recognized by a monoclonal antibody binding to CCR4 produced by hybidoma KM 2160 (FERM BP-10090). The hybidoma KM 2160 has been deposited with International Patent Organism Depositary, National Institute of Advanced Industrial Science and Technology, Central 6, 1-1, Higashi 1-chome, Tsukuba-shi, Ibaraki, Japan, on Aug. 12, 2004 with accession No. FERM BP-10090.

The antibody in the present invention is preferably an antibody low binding activity to a peptide in which at least one tyrosine residues at positions 16, 19, 20 and 22 is sulfated in the peptide comprising positions 13 to 25 of the amino acid sequence represented by SEQ ID NO.1 than a binding activity to a peptide comprising 13 to 25 of the amino acid sequence represented by SEQ ID No. 1.

The antibody in the invention also includes an antibody produced by lectin-resistant cells recognizing a sugar chain structure in which 1-position of fucose is bound to 6-position of N-acetylglucosamine in the reducing end through α-bond in a complex type N-glycoside-linked sugar chain (WO 02/31140, WO 03/85118 and WO 03/85107).

A recombinant antibody of the present invention includes a humanized antibody, human antibody, and the like.

Examples of the humanized antibody are a human chimeric antibody, a human CDR-grafted antibody, and the like.

The human chimeric antibody refers to an antibody comprising H chain V region (hereinafter also referred to as HV or VH) of an antibody of a non-human animal, and L chain V region (herein after also referred to as LV or VL) of an antibody, and CH of human antibody and L chain C region (hereinafter also referred to as CL) of a human antibody. As the non-human animal, any animal can be used so long as hybridomas can be prepared from the animal. Suitable animals include mouse, rat, hamster, rabbit and the like.

The human chimeric antibody of the present invention can be produced by obtaining cDNAs encoding VH and VL from a hybridoma capable of producing a monoclonal antibody derived from non-human animal which specifically reacts with CCR4, inserting them into an expression vector for animal cell having genes encoding human antibody CH and human antibody CL to thereby construct a vector for expression of human chimeric antibody, and then introducing the vector into a host cell to express the antibody.

Any CH of a human chimeric antibody can be used, so long as it belongs to human immunoglobulin (hereinafter referred to as hIg), but those of IgG class are preferred, and any one of subclasses further belonging to IgG such as γ1, γ2, γ3 and γ4 can be used. Also, as CL of a human chimeric antibody, those of κ class or λ class can be used.

The human chimeric antibody of the present invention is a human chimeric antibody which comprises CDR1, CDR2 and CDR3 of VH comprising the amino acid sequences represented by SEQ ID NOs:5, 6 and 7, respectively, and CDR1, CDR2 and CDR3 of VL comprising the amino acid sequences represented by SEQ ID NOs:8, 9 and 10, respectively. Specifically, it includes a human chimeric antibody which comprises VH and VL comprising the amino acid sequences represented by SEQ ID NOs:11 and 12, respectively. More specifically, it includes a human chimeric antibody wherein the VH of the antibody consists of the amino acid sequence represented by SEQ ID NO: 11, the H chain C region of the human antibody consists of an amino acid sequence of the hIgG1 subclass, the L chain V region consists of the amino acid sequence represented by SEQ ID NO:12, and the L chain C region of the human antibody consists of an amino acid sequence of the κ class. An example includes anti-CCR4 human chimeric antibody KM 2760 disclosed in WO01/64754.

The human CDR-grafted antibody refers to an antibody in which CDRs of VH and VL of an antibody derived from a non-human animal which specifically binds to CCR4 are grafted into appropriate sites in VH and VL of a human antibody.

The human CDR-grafted antibody of the present invention can be produced by constructing cDNAs encoding V regions in which CDRs of VH and VL of a non-human animal-derived antibody which specifically binds to CCR4 are grafted into FR of VH and VL of an arbitrary human antibody, inserting the resulting cDNAs into an expression vector for animal cells which has DNAs encoding the CH and the L chain C region (hereinafter referred to as CL) of a human antibody, respectively, to construct a human CDR-grafted antibody expression vector, and introducing the expression vector into an animal cell to induce expression.

As the method for selecting the amino acid sequences of frameworks (hereinafter referred to as FR) of VH and VL of a human antibody, any of those derived from human antibodies can be used. Suitable sequences include the amino acid sequences of FRs of VH and VL of human antibodies registered in databases such as Protein Data Bank, and the amino acid sequences common to each subgroup of FRs of VH and VL of human antibodies (Sequences of Proteins of Immunological Interest, U.S. Dept. Health and Human Services, 1991).

As the CH for the antibody of the present invention, any CH of antibodies can be used, so long as it belongs to human immunoglobulin (hereinafter referred to as hIg), but those of IgG class are preferred, and any one of subclasses further belonging to IgG such as γ1, γ2, γ3 and γ4 can be used. Also, as CL of a human chimeric antibody, those of κ class or λ class can be used.

An example of the human CDR-grafted antibody of the present invention is a human CDR-grafted antibody or antibody fragment comprising CDR1, CDR2 and CDR3 of VH of the antibody consisting of the amino acid sequences represented by SEQ ID NOs: 5, 6 and 7, respectively; and/or CDR1, CDR2 and CDR3 of VL of the antibody consisting of the amino acid sequences represented by SEQ ID NOs:8, 9 and 10, respectively.

Preferred examples include a human CDR-grafted antibody, wherein the VH of the antibody comprises the amino acid sequence represented by SEQ ID NO: 13 or 14, and/or VL of the antibody comprises the amino acid sequence represented by SEQ ID NO: 15.

More Preferable examples include:

a human CDR-grafted antibody which comprises VH of the antibody comprising an amino acid sequence in which at least one or more amino acid residue selected from Ala at position 40, Gly at position 42, Lys at position 43, Gly at position 44, Lys at position 76 and Ala at position 97 in the amino acid sequence represented by SEQ ID NO.13 is replaced with another amino acid residue;

a human CDR-grafted antibody which comprises VH of the antibody comprising an amino acid sequence in which at least one or more amino acid residue selected from Thr at position 28 and Ala at position 97 in the amino acid sequence represented by SEQ ID NO. 14 is replaced with another amino acid residue;

a human CDR-grafted antibody which comprises VL of the antibody comprising an amino acid sequence in which at least one or more amino acid residue selected from Ile at position 2, Val at position 3, Gln at position 50 and Val at position 88 in the amino acid sequence represented by SEQ ID NO. 15 is replaced with another amino acid residue;

a human CDR-grafted antibody which comprises VH of the antibody comprising an amino acid sequence in which at least one or more amino acid residue selected from Ala at position 40, Gly at position 42, Lys at position 43, Gly at position 44, Lys at position 76, and Ala at position 97 is replaced with another amino acid residue in the amino acid sequence represented by SEQ ID NO.13, and VL of the antibody comprising an amino acid sequence in which at least one or more amino acid residue selected from Ile at position 2, Val at position 3, Gln at position 50 and Val at position 88 in the amino acid sequence represented by SEQ ID NO. 15 is replaced with another amino acid residue; and A human CDR-grafted antibody which comprises VH of the antibody comprising an amino acid sequence in which at least one or more amino acid residue selected from Thr at position 28 and Ala at position 97 in the amino acid sequence represented by SEQ ID NO. 14 is replaced with another amino acid residue, and VL of the antibody comprising an amino acid sequence in which at least one or more amino acid residue selected from Ile at position 2, Val at position 3, Gln at position 50 and Val at position 88 in the amino acid sequence represented by SEQ ID NO.15 is replaced with another amino acid residue.

Still more preferable examples include a CDR-grafted antibody which comprises the heavy chain (H chain) variable region (V region) of the antibody comprising the amino acid sequence represented by SEQ ID NO:16 or 17 and the light chain (L chain) V region of the antibody molecule comprising the amino acid sequence represented by SEQ ID NO: 18, and the like.

Also included within the scope of the present invention are antibodies or antibody fragments which specifically react with CCR4 and consist of amino acid sequences wherein one or more amino acid residues are deleted, added, substituted or inserted in the above amino acid sequences.

The expression "one or more amino acid residues are deleted, substituted, inserted or added in the amino acid sequence in the present invention" means that one or more amino acids are deleted, substituted, inserted, or added at single or plural arbitrary position (s) in the amino acid sequence. Deletion, substitution, insertion and addition may be caused in the same amino acid sequence simultaneously and amino acid residues to be substituted, inserted or added may be either natural or non-natural. Examples of the natural amino acid residues are L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The followings are preferred examples of the amino acid residues capable of mutual substitution. The amino acid residues in the same group shown below can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine Specific examples of the human CDR-grafted antibody in the invention include a human CDR-grafted antibody described in WO 03/18635, a human CDR-grafted antibody prepared from monoclonal antibody 1G1, 2B10 or 10E4 as described in WO 00/42074, a human CDR-grafted antibody prepared from a humanized antibody or monoclonal antibody 252Y or 252Z as described in WO 99/15666, a human CDR-grafted antibody prepared from a monoclonal antibody as described in U.S. Pat. No. 6,245,332.

The human antibody originally means an antibody naturally existing in the human body. However, it also includes antibodies obtained from a human antibody phage library and human antibody-producing transgenic animals prepared by the recent advance in genetic engineering, cell engineering and developmental engineering techniques, and the like.

With respect to the antibody naturally existing in the human body, for example, human peripheral blood lymphocytes are isolated, infected with EB virus or the like for immortalization and cloning, whereby lymphocytes producing the antibody can be cultured, and the antibody can be purified from the cultures.

The human antibody phage library is a library in which an antibody gene prepared from a human B cell is inserted into a phage gene to express an antibody fragment such as Fab or scFv on the surface of the phage. A library in which mutation is artificially introduced can be used to develop the library. From the library, a phage having a desired antigen binding activity can be recovered using a binding activity to a substrate having an antigen immobilized thereon as an index. The antibody fragment can further be converted to a human antibody molecule comprising two full length H chains and two full length L chains by a protein engineering method.

The human antibody-producing transgenic animal means an animal in which a human antibody gene is incorporated into cells. Specifically, a human antibody-producing transgenic mouse prepared by introducing a human antibody gene into a mouse ES cell, grafting the ES cell on an early embryo of the mouse and developing the same, and the like are mentioned. Regarding the method for preparing a human antibody from the human antibody-producing transgenic animal, the human antibody can be produced and accumulated in a culture supernatant by culturing a human antibody-producing hybridoma obtained by a hybridoma preparation method generally carried out in cell fusion method.

Examples of transgenic non-human animals include cattle, sheep, goats, pigs, horses, mice, rats, chickens, monkeys, rabbits and the like.

An antibody fragment of the present invention includes Fab, Fab', F(ab')$_2$, scFv, Diabody, dsFv, and a peptide comprising CDR. An Fab is an antibody fragment having a molecular weight of about 50,000 and having an antigen-binding activity, in which about a half of the N-terminal side of H chain and the full length L chain, among fragments obtained by treating an IgG type antibody molecule with a protease, papain (cleaving at the amino acid residue at position 224 of the H chain), are bound together through a disulfide bond (S—S bond).

The Fab of the present invention can be obtained by treating the human CDR-grafted antibody of the present invention which specifically reacts with human CCR4, with the protease, papain. Alternatively, the Fab may be produced by inserting DNA encoding the Fab of the antibody into an expression vector for prokaryote or eukaryote, and introducing the vector into a prokaryote or eukaryote to induce expression.

An F(ab')₂ is an antibody fragment having a molecular weight of about 100,000 and having an antigen-binding activity, which is slightly larger than the Fab bound via a S—S bond at the hinge region, among fragments obtained by treating an IgG-type antibody molecule with a protease, pepsin (cleaving at the amino acid residue at position 234 of the H chain).

The F(ab')₂ of the present invention can be obtained by treating the human CDR-grafted antibody of the present invention which specifically reacts with human CCR4 with the protease, pepsin. Alternatively, the F(ab')₂ may be prepared by binding Fab' fragments described below by a thioether bond or a S—S bond.

An Fab' is an antibody fragment with a molecular weight of approximately 50,000 having antigen-binding activity, which is obtained by cleaving S—S bond at the hinge region of the above F(ab')₂.

The Fab' of the present invention can be obtained by treating the F(ab')₂ of the present invention which specifically binds to human CCR4 with a reducing agent, dithiothreitol. Alternatively, the Fab' may be produced by inserting DNA encoding the Fab' of the human CDR-grafted antibody which specifically reacts with CCR4 into an expression vector for prokaryote or eukaryote, and introducing the vector into a prokaryote or eukaryote to induce expression.

An scFv is a VH-P-VL or VL-P-VH polypeptide in which one chain VH and one chain VL are linked by using an appropriate peptide linker (P) of 12 or more amino acid residues and which has an antigen-binding activity.

The scFv of the present invention can be produced by obtaining cDNAs encoding the VH and VL of the human CDR-grafted antibody which specifically binds to CCR4, constructing DNA encoding the scFv, inserting the DNA into an expression vector for prokaryote or eukaryote, and introducing the expression vector into a prokaryote or eukaryote to induce expression.

A diabody is an antibody fragment in which scFv having the same or different antigen binding specificity forms a dimer, and has an divalent antigen binding activity to the same antigen or two specific antigen binding activity to different antigens.

The diabody of the present invention, for example, a divalent diabody which specifically binds to CCR4, can be produced by obtaining cDNAs encoding VH and VL of the human CCR4-grafted antibody which binds specifically to CCR4, constructing DNA encoding scFv having a polypeptide linker of 3 to 10 amino acid residues, inserting the DNA into an expression vector for prokaryote or an expression vector for eukaryote; and then introducing the expression vector into a prokaryote or eukaryote to express the diabody.

A dsFV is an antibody fragment which is obtained by binding polypeptides in which one amino acid residue of each of VH and VL is substituted with a cysteine residue and those cysteine residues are bound via a S—S bond between the cysteine residues. The amino acid residue which is substituted with a cysteine residue can be selected based on a three-dimensional structure estimation of the antibody in accordance with the method shown by Reiter et al. (Protein Engineering, 7, 697 (1994)).

The dsFv of the present invention can be produced by obtaining cDNAs encoding VH and VL of the human CCR4-grafted antibody which specifically binds to CCR4, constructing DNA encoding dsFv, inserting the DNA into an expression vector for prokaryote or expression vector for eukaryote, and then introducing the expression vector into a prokaryote or eukaryote to express the dsFv.

A peptide comprising CDR comprises one or more region of CDRs of VH and VL. The peptide comprising plural CDRs can be produced by binding directly to or via an appropriate peptide linker.

The peptide comprising CDR of the present invention can be produced by constructing cDNAs encoding CDR of VH and VL of the human CCR4-grafted antibody which specifically binds to CCR4, inserting the cDNAs into an expression vector for prokaryote or an expression vector for eukaryote, and then by introducing the expression vector into a prokaryote or eukaryote to express the peptide. Also, the peptide comprising CDR can be produced by a chemical synthesis method such as an Fmoc method (fluorenylmethoxycarbonyl method), a tBoc method (t-butyloxycarbonyl method), or the like.

Agents used in the present invention include protein, agent having low molecular weight, and the like.

Examples of proteins include cytokines, antibodies and the like.

The cytokines include cytokines which activate the effector cells such as NK cells, macrophages, monocytes, granulocytes, which are immunocompetent cells. Specific examples of the cytokines include interleukin 2 (IL-2), IFN-α, IFN-γ, IL-12, IL-15, IL-18, IL-21, fractalkine, M-CSF, GM-CSF, G-CSF, TNF-α, TNF-β, IL-1α, IL-1β, and the like.

Examples of antibodies include antibody, antibody fragment and fusion antibody which specifically react with surface markers of T cell. Specific antibodies include anti-CD3 antibody (Orthoclone), anti-CD4 antibody, anti-CD5 antibody, anti-CD8 antibody, anti-CD30 antibody, anti-CD2 antibody, anti-CD25 antibody (Zenapax, Hoffmann-La Roche Inc.), anti-CD52 antibody (Campath, Ilex Oncology, Inc.), and the like.

Examples of the agent having low molecular weight of the present invention include amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, Methotrexate, 5-fluorouracil, vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), floxuridine, fludarabine, hydroxyurea, ifosfamide, idarubicin, mesna, irinotecan, mitoxantrone, topotecan, leuprolide, megestrol, melpharan, mercaptopurine, plicamycin, mitotane, pegaspargase, pentostatin, pipobroman, streptozocin, tamoxifen, teniposide, testolactone, thioguanine, thiotepa, uracil mustard, vinorelbine, chlorambucil, prednisolone, vindesine, nimstine, semustin, capecitabine, tomudex, azacytidine, UFT, oxaloplatin, gefitinib (Iressa), imatinib (STI571), amsacrine, all-trans retinoic acid, thalidomide, bexarotene (targretin), dexamethasone, anastrozole (Alimidex), leuplin or combined use thereof. Preferable examples include vincristine, cyclophosphamide, etoposide, Methotrexate or combined use thereof.

When the above agent is administered in vivo solely at a high dose, fear of possible side effect may arose. However, in the present invention, the above agent can be used at a low dose by being combined with the recombinant antibody which specifically binds to CCR4 or the antibody fragment thereof. Accordingly, in addition to the satisfactory therapeutic effect, the side effect can be reduced.

The medicament of the invention can be used against cells in which CCR4 is expressed. Tumor cells are preferable. Specifically, a hematopoietic organ tumor is mentioned as the tumor.

The hematopoietic organ tumor includes acute leukemia, chronic leukemia, Hodgkin's disease, non-Hodgkin's disease and the like.

Examples of the acute leukemia include acute lymphatic leukemia and the like, and examples of the acute lymphatic leukemia include pre-T cell acute lymphatic leukemia and the like.

The chronic leukemia includes chronic lymphatic leukemia. Examples of the chronic lymphatic leukemia include T cell chronic lymphatic leukemia, T cell pre-lymphatic leukemia, adult T cell leukemic lymphoma (ATL), Sezary syndrome and the like.

The non-Hodgkin's disease includes T/NK cell lymphoma. Examples of the T/NK cell lymphoma include pre-T lymphoblast lymphoma/leukemia, mature T cell tumor and the like.

Examples of the mature T cell tumor include T cell pre-lymphocyte leukemia, T cell large granular lymphocyte leukemia, Sezary syndrome, mycosis fungoides, primary skin undifferentiated large cell lymphoma, subcutaneous phlegmon-like T cell lymphoma, intestinal disease-type bowel T cell lymphoma, liver/spleen γδ T cell lymphoma, angioimmunoblastic T cell lymphoma, peripheral T cell lymphoma, undifferentiated large cell lymphoma, adult T cell leukemia/lymphoma and the like.

The effect of the medicament of the present invention can be measured by an in vitro cytotoxic activity measuring method. As the in vitro cytotoxic activity measuring method, an ADCC measuring system is mentioned. ADCC can be measured by contacting target cells expressing CCR4 as an antigen with effector cells such as peripheral blood mononuclear cells, monocytes, macrophages or granulocytes collected from humans or other animals, detecting a degree of damaged target cells, and determining the same. The degree of damaged target cells can be detected by a $^{51}$Cr release method, a method for detecting an enzyme activity of target cells, a detecting method using a flow cytometer, or the like. The effect of the medicament of the present invention in the ADCC measuring system can be measured by adding the agent to the ADCC measuring system or exposing these agents to the target cells or the effector cells or both of them for a prescribed period of time and observing influences exerted on ADCC.

The effect of the medicament of the present invention may be examined by measuring an in vivo antitumor activity using animal models.

Examples of the animal models include xenograft models obtained by grafting a culture cell line derived from a human cancer tissue in immunodeficient mice such as nude mice, isograft models obtained by grafting a cultured mouse cancer cell line in wild-type mice having a normal immune system, and the like.

The xenograft models can be prepared by grafting a human cancer cell line in various sites such as subcutaneous, intracutaneous, intraperitoneal and intravenous sites of immunodeficient mice such as nude mice.

The isograft models for evaluation of the medicament of the present invention can be prepared by introducing a CCR4 gene into a mouse culture cell line such as EL4 cell to form a CCR4-positive transformant and grafting this transformant into various sites of wild-type mice having a normal immune system.

The effect of the medicament of the present invention can be evaluated by comparing an effect of administration of the antibody alone or an effect of administration of the agent alone with an effect of the medicament of the present invention using the animal models.

The medicament of the present invention can be administered alone, but it is generally preferred to provide it in the form of a pharmaceutical preparation produced by mixing it with one or more pharmaceutically acceptable carriers in accordance with any method well known in the technical field of pharmaceutics.

It is preferable to select a route of administration which is most effective in treatment. Examples include oral administration and parenteral administration, such as intraoral, tracheobronchial, intrarectal, subcutaneous, intramuscular and intravenous. In an protein preparation, intravenous administration is preferred.

Examples of the preparation suitable for the oral administration are spray, capsule, tablet, granule, syrup, emulsion, suppository, injection, ointment, tape and the like.

Liquid preparation such as emulsion and syrup can be produced using water, saccharides such as sucrose, sorbitol and fructose, glycols such as polyethylene glycol and propylene glycol, oils such as sesame oil, olive oil and soybean oil, antiseptics such as p-hydroxybenzoate, flavors such as strawberry flavor and peppermint flavor and the like, as additives.

Capsule, tablet, diluted powder, granule, and the like can be produced using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid ester, plasticizers such as glycerol, as additives.

Examples of the preparation suitable for parenteral administration are injection, suppository, air spray and the like.

Suppository is prepared using a carrier such as cacao butter, hydrogenated fat or carboxylic acid.

Air spray is prepared using the medicament as such or using, for example, a carrier which does not stimulate the mouth and the airway mucous membrane of a person to be administered, and which disperses the medicament into fine particles and makes the absorption easy.

Specific examples of the carrier are lactose and glycerol. Depending upon the property of the medicament and the carrier used, it is possible to prepare aerosol, dry powder, and the like. In addition, even in the parenteral preparation, components exemplified as additives in the oral preparation may be added.

A dose or an administration schedule vary depending on a desired therapeutic effect, an administration method, a therapeutic period, an age, a body weight and the like. The dose of the antibody in one administration is usually from 0.1 to 20 mg/kg for an adult. The agent used in combination with the antibody is administered at a dose equal to or lower than the dose when the agent is used alone in clinic.

Figure 1:
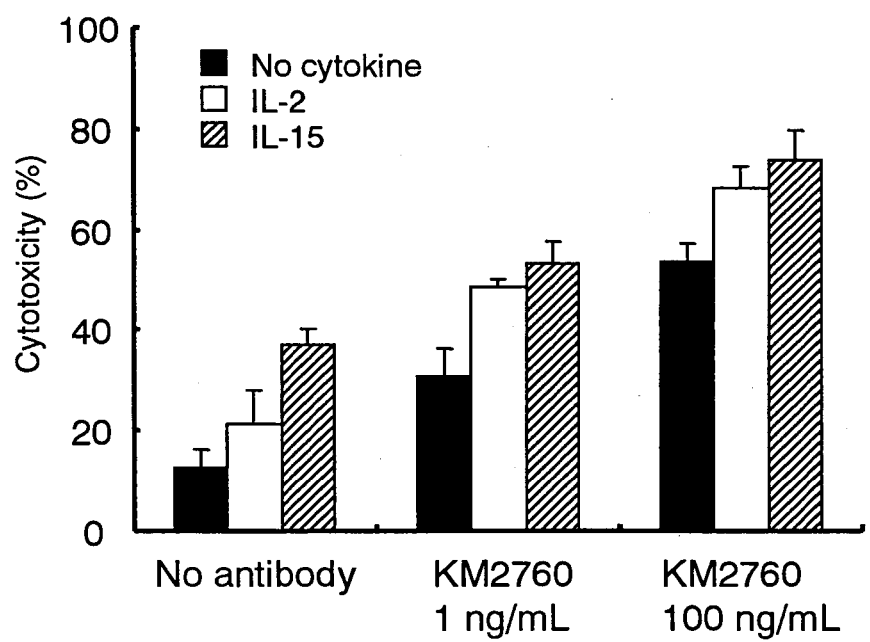
FIG. 1 shows an enhancement effect of a cytokine against a cytotoxic activity of an anti-CCR4 antibody. The ordinate shows a cytotocity. ■ indicates a cytotoxic activity without addition of cytokine, □ indicates a cytotoxic activity in addition of IL-2, and a hatch indicates a cytotoxic activity in addition of IL-15 respectively. A bar indicates a standard deviation.

The present invention is described in detail below. The present application claims the Convention priority from Japanese Patent Application Nos. 2003-406590 and 2004-155141 filed Dec. 4, 2003 and May 25, 2004, including the contents described in the specifications and/or drawings of these applications.

BEST MODE FOR CARRYING OUT THE INVENTION

Example 1

Effect of an Anti-CCR4 Antibody and a Cytokine in Combination in an In Vitro Cytotoxic Activity An effect of using anti-CCR4 human chimeric antibody KM 2760 (FERM BP-7054, WO 01/64754) and a cytokine in combination in an in vitro cytotoxic activity was measured by the following method.

(a) Preparation of an Effector Cell Suspension

A vein blood (50 mL) was collected from a healthy person, 0.5 mL of heparin sodium (manufactured by Shimizu Seiyaku K.K.) was added, and they were gently mixed. A mononuclear cell layer was separated from using a MONO-POLY separation solution (manufactured by Dainippon Pharmaceutical Co., Ltd.) according to the attached manual. After the layer was subjected to centrifugation and washed with RPMI 1640-FCS (5) medium [RPMI 1640 medium containing 5% FCS (Gibco. BRL)] for three times, the cells were resuspended in the same medium to a concentration of $3 \times 10^6$ cells/ml to give an effector cell suspension.

(b) Stimulation of Effector Cells by a Cytokine

The effector cell suspension obtained in the above (a) was dispensed at 50 μl/well in a 96-well U-bottom plate (manufactured by Falcon) in an amount of 50 μl/well. Further, either 50 μL of a 2 ng/mL IL-2 (manufactured by Peprotech) solution diluted with RPMI 1640-FCS(5) medium, 50 μL of a 2 ng/mL of IL-15 (manufactured by Peprotech) solution or 50 μL of RPMI 1640-FCS(5) as a negative control without addition of a cytokine were added to separate samples, and were allowed to stand still in a 5% $CO_2$ incubator for 3 days.

(c) Preparation of a Target Cell Suspension

CCR4/EL4 cells (WO01/64754) which are transformant tumor cells obtained by introducing a human CCR4 gene into mouse thymoma cell line EL4 were cultured in RPMI 1640-FCS(10) medium [RPMI 1640 medium containing 10% FCS (manufactured by Gibco BRL)] containing 0.5 mg/mL of G418 (manufactured by Nacalai Tesque) washed with RPMI 1640-FCS(5) medium subjected to centrifugation and suspension, and then adjusted to a concentration of $2 \times 10^5$ cells/mL with RPMI 1640-FCS(5) medium to form a target cell suspension.

(d) Measurement of a Cytotoxic Activity

The target cell suspension (50 μL) prepared in the above (c) was added to each well of a 96-well U-shaped bottom plate containing the effector cells stimulated with the cytokine in the above (b) such that the concentration became $1 \times 10^4$ cells/well. At this time, the effector cell:target cell ratio is 15:1. Further, KM 2760 was added such that the final concentration became 1 or 100 ng/mL to each well was allowed to react, and at 37° C. for 4 hours. After the reaction, the plate was subjected to centrifugation, and a lactic acid dehydrogenase (hereinafter referred to as LDH) activity in the supernatant was measured by obtaining an absorbance data with Cyto-Tox96 Non-Radioactive Cytotoxic activity Assay (manufactured by Promega) according to the attached manual. An absorbance data of target cell spontaneous release was obtained by the same procedure as above using RPMI 1640-FCS(5) medium in the same volume instead of the effector cell suspension and the antibody solution, and absorbance data of effector cell spontaneous release was obtained by the same procedure as above using RPMI 1640-FCS(5) medium in the same volume instead of the target cell suspension and the antibody solution. With respect to an absorbance data of target cell total release, a reaction was conducted using RPMI 1640-FCS(5) medium in the same volume instead of the antibody solution and the effector cell solution, 15 μL of a 9% Triton X-100 solution was added 45 minutes before completion of the reaction, and the same procedure as above was conducted to measure an LDH activity of the supernatant. ADCC was obtained using the following formula.

Cytotoxic activity (%)=[(absorbance of a specimen)−(absorbance of effector cell spontaneous release)−(absorbance of target cell spontaneous release)]/[(absorbance of target cell total release)−(absorbance of target cell spontaneous release)]×100          (Formula 1)

The results were shown in FIG. 1. The cytotoxic activity of KM 2760 was increased in a concentration-dependent manner. It was more increased by addition of the cytokine. The results show that the cytotoxic activity of the anti-CCR4 antibody is enhanced by the cytokine that activates the effector cells.

Example 2

Antitumor Effect Provided by Administrating an Anti-CCR4 Antibody and Vincristine in Combination CCRF-CEM cells (human T cell leukemia cell line) were suspended in RPMI 1640 medium (Gibco BRL) at a concentration of $2 \times 10^8$ cells/mL, and 100 μL of the suspension was grafted into the ventral skin of Balb/c nude mouse (Nippon Crea, male). On Day 15 after the cell grafting, a diameter of a tumor was measured with calipers, and a tumor volume was calculated using the following formula.

Tumor volume=short diameter×short diameter×long diameter×0.5 (Formula 2)

Individuals having the tumor volume within the range of 140 to 342 mm$^3$ (on average 260 mm$^3$) were selected, and grouped such that the average of tumor volume to be almost the same. Each of following agents A to D was administered to the mice. Incidentally, the grouping day was defined as Day 0.

A. Negative control group: No administration
B. Group of administering KM 2760 alone: 800 μg of KM2760 was administered per mouse on Day 0 and Day 4.
C. Group of administering vincristine (hereinafter referred to as VCR; Oncovin injection, Eli Lilly Japan K.K.) alone: 0.55 mg/kg of VCR was administered per mouse on Day 0.
D. Group of administering KM 2760 and VCR in combination: 0.55 mg/kg of VCR was administered per mouse on Day 0, and 800 μg of KM 2760 was administered per mouse on Day 0 and Day 4.

The experiment was conducted with groups each consisting of five mice. Each of the agents was diluted with a physiological saline (Otsuka Seiyaku), and the diluent was administered from the tail vein. On Day 10, the tumor volume was measured. The antitumor effect was evaluated by comparing average values of a tumor volume change (V/V0) on Day 10 when the tumor volume on Day 0 in each group was defined as V0.

Figure 2:
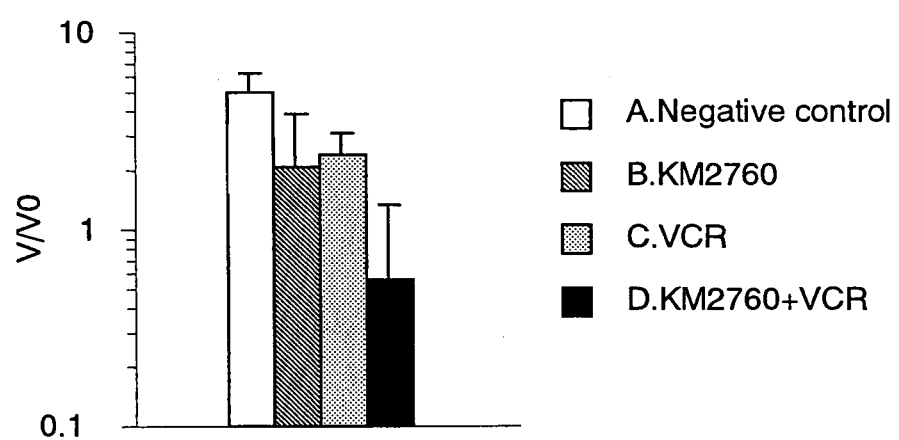
FIG. 2 indicates an effect provided by combined use of an anti-CCR4 antibody and vincristine against CCRF-CEM cells grafted in a nude mouse. The ordinate shows a V/V0 value. □ indicates a V/V0 value of a negative control group, a slashed bar indicates a V/V0 value of KM 2760 administration group, a gray indicates a V/V0 value of a vincristine administration group, and ■ indicates a V/V0 value of a group of administrating KM 2760 and vincristine in combination, respectively. A bar indicates a standard deviation.

The average values of V/V0 in each group is shown in FIG. 2. As shown in FIG. 2, the administration of KM 2760 and VCR in combination exhibited the higher effect for suppressing growth than the administration of VCR or the antibody alone.

A value (T/C) obtained by dividing V/V0 of each group by V/V0 of the negative control group is shown in Table 1. In comparison with a theoretical value of T/C when simply adding the pharmaceutical effects of both KM 2760 and VCR, namely, a value obtained by multiplying T/Cs of the groups of administering the respective agents alone, actual T/C of the combined administration group (C in the table) exhibited the lower value (0.11) than 0.21, the theoretical value on Day 10.

TABLE 1

| T/C of each group | | | | |
|---|---|---|---|---|
| A. Negative control | B. KM 2760 | C. VCR | D. KM 2760 + VCR | Theoretical Value (B × C) |
| 1 | 0.43 | 0.49 | 0.11 | 0.21 |

From the foregoing, it has been clarified that the administration of KM 2760 and VCR in combination has the higher antitumor effect than the administration of KM 2760 or VCR alone, and exhibits the synergistic effect.

Example 3

Antitumor Effect Provided by Administrating an Anti-CCR4 Antibody and Cyclophosphamide in Combination CCRF-CEM cells (human T cell leukemia cell line) were suspended in RPMI 1640 medium (Gibco BRL) at a concentration of $2 \times 10^8$ cells/mL, and 100 μL of the suspension was grafted intradermally in the right flank of Balb/c nude mice (Nippon Crea, male). On Day 18 after the cell grafting, a diameter of a tumor was measured with calipers, and a tumor volume was calculated using formula 2 in Example 2.

Individuals having the tumor volume within the range of 116 to 349 mm$^3$ (on average 219 mm$^3$) were selected, and grouped such that the average tumor volume to be almost the same. Each of the following agent A to D was administered to the mice. Incidentally, the grouping day was defined as Day 0.

A. Negative control group: No administration
B. Group of administering KM 2760 alone: 800 μg of KM2760 was administered per mouse on Day 0 and Day 4.
C. Group of administering cyclophosphamide (hereinafter referred to as CPA; Endoxan for injection, Baxter) alone: 65 mg/kg of CPA was administered per mouse on Day 0.
D. Group of administering KM 2760 and CPA in combination: 65 mg/kg of CPA was administered per mouse on Day 0, and 800 μg of KM 2760 was administered per mouse on Day 0 and Day 4.

The experiment was conducted with groups each consisting of five mice. Each of the agents was diluted with a physiological saline (Otsuka Seiyaku), and the diluent was administered from the tail vein. On Day 4, the tumor volume was measured. The antitumor effect was evaluated by comparing an average values of a tumor volume change (V/V0) on each measurement day when the tumor volume on Day 0 in each group was defined as V0.

Figure 3:
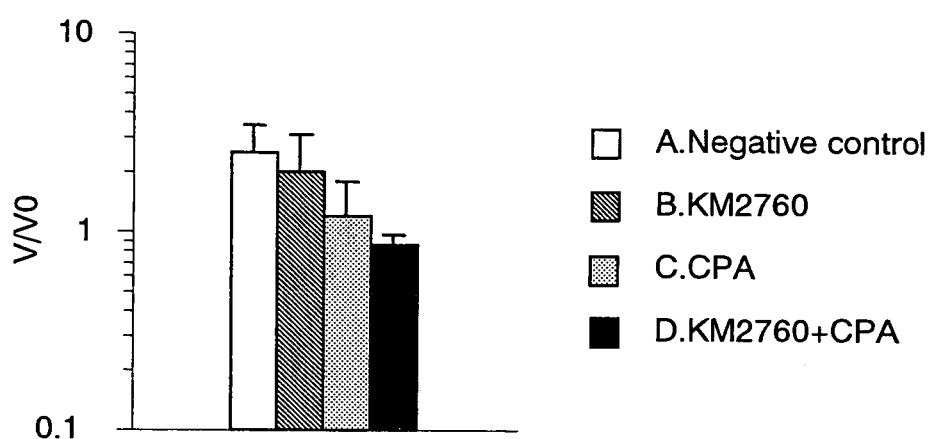
FIG. 3 indicates an effect provided by combined use of an anti-CCR4 antibody and cyclophosphamide against CCRF-CEM cells grafted in a nude mouse. The ordinate shows a V/V0 value. □ indicates a V/V0 value of a negative control group, a slashed bar indicates a V/V0 value of a KM 2760 administration group, a gray indicates a V/V0 value of a cyclophosphamide administration group, and ■ indicates a V/V0 value of a group of administration of KM 2760 and cyclophosphamide in combination, respectively. A bar indicates a standard deviation.

The chronological change in average values of V/V0 in each group is shown in FIG. 3. As shown in FIG. 3, the administration of KM 2760 and CPA in combination exhibited the higher effect for suppressing growth than the administration of CPA or the antibody alone.

A value (T/C) obtained by dividing V/V0 of each group by V/V0 of the negative control group is shown in Table 2. In comparison with a theoretical value of T/C when simply adding the pharmaceutical effects of both KM 2760 and CPA, namely, a value obtained by multiplying T/Cs of the groups of administering the respective agents alone, actual T/C of the combined administration group (D in the table) exhibited the lower value (0.35) than 0.39, the theoretical value.

TABLE 2

| T/C of each group | | | | |
|---|---|---|---|---|
| A. Negative control | B. KM 2760 | C. CPA | D. KM 2760 + CPA | Theoretical Value (B × C) |
| 1.00 | 0.80 | 0.48 | 0.35 | 0.39 |

From the foregoing, it has been clarified that the administration of KM2760 and CPA in combination has the higher antitumor effect than the administration of KM2760 or CPA alone, and exhibits the synergistic effect.

Example 4

Antitumor Effect Provided by Administrating an Anti-CCR4 Antibody and Etoposide in Combination CCRF-CEM cells (human T cell leukemia cell line) were suspended in RPMI 1640 medium (Gibco BRL) at a concentration of $2 \times 10^8$ cells/mL, and 100 μL of the suspension was grafted into the ventral skin of Balb/c nude mice (Nippon Crea, male). On Day 17 after the cell grafting, a diameter of a tumor was measured with calipers, and a tumor volume was calculated using formula 2 in Example 2.

Individuals having the tumor volume within the range of from 121 to 348 mm³ (on average 195 mm³) were selected, and grouped such that the average tumor volume to be almost the same. Each of the following agents A to D was then administered to the mice. Incidentally, the grouping day was defined as Day 0.

A. Negative control group: No administration

B. Group of administering KM 2760 alone: 800 μg of KM2760 was administered per mouse on Day 0 and Day 4.

C. Group of administering etoposide (hereinafter referred to as VP-16; Lastet injection, Nippon Kayaku Co., Ltd.) alone: 10 mg/kg of VP-16 was administered per mouse for 5 days from Day 0 to Day 4.

D. Group of administering KM2760 and VP-16 in combination: 10 mg/kg of VP-16 was administered per mouse for 5 days from Day 0 to Day 4, and 800 μg of KM 2760 was administered per mouse on Day 0 and Day 4.

The experiment was conducted with groups each consisting of five mice. Each of the agents was diluted with a physiological saline solution (Otsuka Seiyaku), and the diluent was administered from the tail vein. On Day 7, the tumor volume was measured. The antitumor effect was evaluated by comparing average values of a tumor volume change (V/V0) on Day 7 when the tumor volume on Day 0 in each group was defined as V0.

Figure 4:
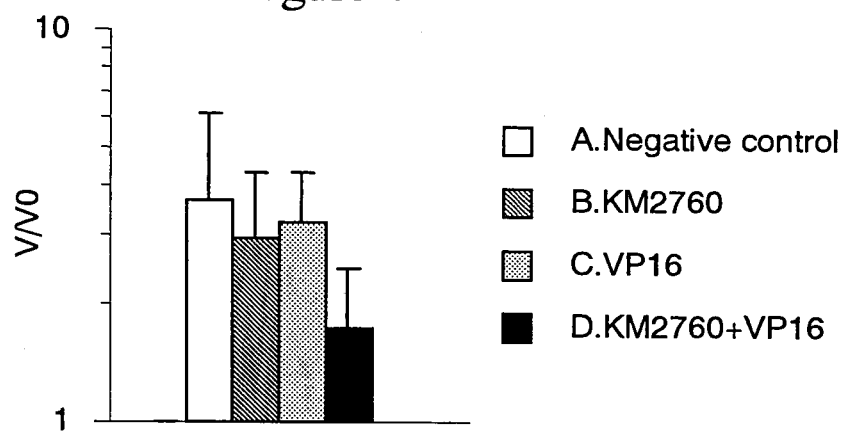
FIG. 4 indicates an effect provided by combined use of an anti-CCR4 antibody and etopiside against CCRF-CEM cells grafted in a nude mouse. The ordinate shows a V/V0 value. □ indicates a V/V0 value of a negative control group, a slashed bar indicates a V/V0 value of a KM 2760 administration group, a gray indicates a V/V0 value of an etoposide administration group, and ■ indicates a V/V0 value of a group administrating KM 2760 and etoposide in combination, respectively. A bar indicates a standard deviation.

The average values of V/V0 in each group is shown in FIG. 4. As shown in FIG. 4, the administration of KM 2760 and VP-16 in combination exhibited the higher effect for suppressing growth than the administration of VP-16 or the antibody alone.

A value (T/C) obtained by dividing V/V0 of each group by V/V0 of the negative control group is shown in Table 3. In comparison with a theoretical value of T/C when simply adding the pharmaceutical effects of both KM 2760 and VP-16, namely, a value obtained by multiplying T/Cs of the groups of administering the respective agents alone, actual T/C of the combined administration group (the value of D in the table) exhibited the lower value (0.38) than 0.46, the theoretical value.

TABLE 3

| T/C of each group | | | | |
|---|---|---|---|---|
| A. Negative control | B. KM 2760 | C. VP-16 | D. KM 2760 + VP-16 | Theoretical Value (B × C) |
| 1.00 | 0.65 | 0.71 | 0.38 | 0.46 |

From the foregoing, it has been clarified that the administration of KM2760 and VP-16 in combination has the higher antitumor effect than the administration of KM2760 or VP-16 alone, and exhibits the synergistic effect.

Example 5

Antitumor Effect Provided by Administrating an Anti-CCR4 Antibody and Methotrexate in Combination CCRF-CEM cells (human T cell leukemia cell line) were suspended in RPMI 1640 medium (Gibco BRL) at a concentration of $2 \times 10^8$ cells/mL, and 100 μL of the suspension was grafted into the ventral skin of Balb/c nude mice (CLEA Japan Inc. male). On Day 17 after the cell grafting, a diameter of a tumor was measured with calipers, and a tumor volume was calculated using formula 2 in Example 2.

Individuals having the tumor volume within the range of 121 to 348 mm³ (on average 195 mm³) were selected, and grouped such that the average tumor volume to be almost the same. Each of the following agents A to D was administered to the mice. Incidentally, the grouping day was defined as Day 0.

A. Negative control group: No administration

B. Group of administering KM 2760 alone: 800 μg of KM2760 was administered per mouse on Day 0 and Day 4.

C. Group of administering Methotrexate (hereinafter referred to as MTX; Methotrexate injection solution, Nippon Weisledary K.K.) alone: 15 mg/kg of MTX was administered per mouse for 5 days from Day 0 to Day 4.

D. Group of administering KM 2760 and MTX in combination: 15 mg/kg of MTX was administered per mouse for 5 days from Day 0 to Day 4, and 800 μg of KM 2760 was administered per mouse on Day 0 and Day 4.

The experiment was conducted with groups each consisting of five mice. Each of the agents was diluted with a physiological saline solution (Otsuka Seiyaku), and the diluent was administered from the tail vein. On Day 7, the tumor volume was measured. The antitumor effect was evaluated by comparing average values of a tumor volume change (V/V0) when the tumor volume on Day 0 in each group was defined as V0.

Figure 5:
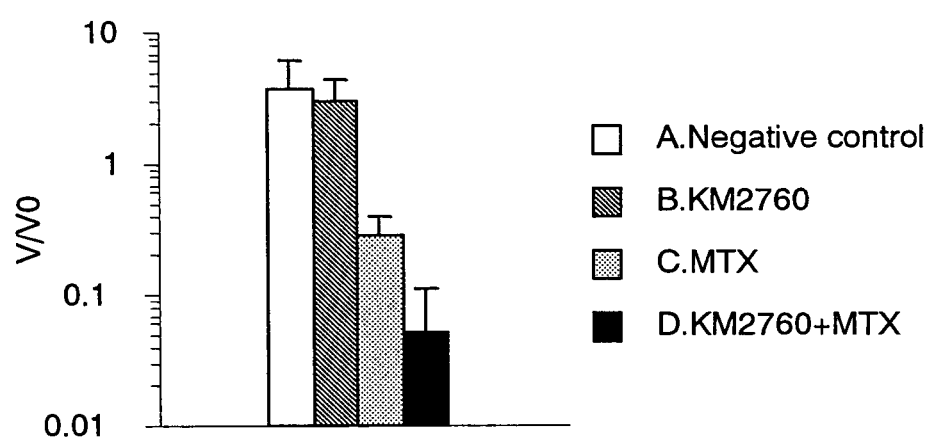
FIG. 5 shows an effect provided by combined use of an anti-CCR4 antibody and Methotrexate against CCRF-CEM cells grafted in a nude mouse. The ordinate shows a V/V0 value. □ indicates a V/V0 value of a negative control group, a slashed bar indicates a V/V0 value of a KM 2760 administration group, a gray indicates a V/V0 value of a Methotrexate administration group, and ■ indicates a V/V0 value of a group administrating of KM 2760 and Methotrexate in combination, respectively. A bar indicates a standard deviation.

The chronological change in average values of V/V0 in each group is shown in FIG. 5. As shown in FIG. 5, the administration of KM 2760 and MTX in combination exhibited the higher effect for suppressing growth than the administration of MTX or the antibody alone.

A value (T/C) obtained by dividing V/V0 of each group by V/V0 of the negative control group is shown in Table 4. In comparison with a theoretical value of T/C when simply adding the pharmaceutical effects of both KM 2760 and MTX, namely, a value obtained by multiplying T/Cs of the groups of administering the respective agents alone, actual T/C of the combined administration group (the value of D in the table 4) exhibited the lower value (0.01) than 0.04, the theoretical value.

TABLE 4

| T/C of each group | | | | |
|---|---|---|---|---|
| A. Negative control | B. KM 2760 | C. MTX | D. KM 2760 + MTX | Theoretical Value (B × C) |
| 1.00 | 0.65 | 0.06 | 0.01 | 0.04 |

From the foregoing, it has been clarified that the administration of KM2760 and MTX in combination has the higher antitumor effect than the administration of KM2760 or MTX alone, and exhibits the synergistic effect.

Example 6

Antitumor Effect Provided by Administrating an Anti-CCR4 Human Chimeric Antibody KM 2760 and G-CSF in Combination CCR4/EL4 Cells (WO 01/64754) were suspended in RPMI 1640 medium (Gibco BRL) at a concentration of $1 \times 10^6$ cells/mL, and 100 μL of the suspension was grafted into the right ventral skin of C57BL/6 mice (Nippon Crea, male, 8 weeks old). After, mice were grouped into A to D, each of the agents A to D were administered to each mouse. Incidentally, the day on which the tumor was grafted was defined as Day 0.

A. Negative control group: No administration

B. Group of administering KM 2760 alone: 100 µg of KM2760 was intravenously administered per mouse on Day 0 and Day 4.

C. Group of administering G-CSF alone: 10 µg of G-CSF (Neuup Injection 100, manufactured by Kyowa Hakko Kogyo Co., Ltd.) was subcutaneously administered per mouse once a day for 10 days from 4 days before the tumor grafting (hereinafter referred to as Day-4) to Day 5. The administration site is near the hind limb on the right ventral portion which does not overlap with the tumor grafting site.

D. Group of administering KM2760 and G-CSF in combination: 100 µg of KM 2760 was intravenously administered per mouse once a day on Day 0 and Day 4, and 10 µg of G-CSF was subcutaneously administered per mouse once a day for 10 days from Day-4 to Day 5. The administration site is near the hind limb on the right ventral portion which does not overlap with the tumor grafting site.

The experiment was conducted with group A consisting of 10 mice and groups B, C and D each consisting of 7 mice. KM 2760 was diluted with a citrate buffer solution (10 mM citric acid, 150 mM sodium chloride, pH 6), and G-CSF was diluted with a physiological saline (Otsuka Seiyaku) respectively. Each of the diluent was administered at 100 µL. A diameter of a tumor was measured with calipers chronologically from Day 0 of each group. A tumor volume was calculated using formula 2 in Example 2.

Since the tumor death of the mouse was started in group A from Day 17 on, the evaluation of the tumor volume was finished on Day 14.

Figure 6:
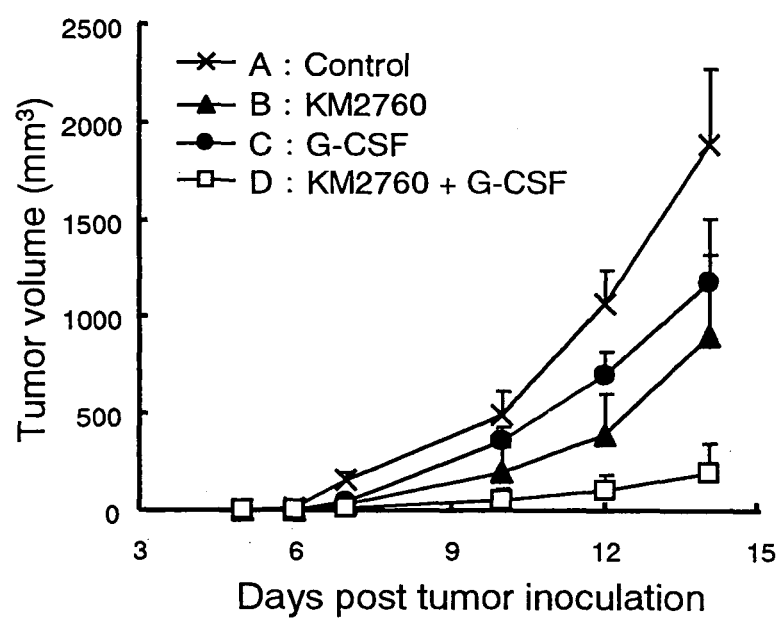
FIG. 6 shows an effect provided by combined use of an anti-CCR4 antibody and G-CSF against CCR4/EL4 cells grafted in C57BL/6 mouse. The abscissa shows the number of days after grafting the tumor, the ordinate shows a tumor volume respectively. X indicates a negative control group, ▲ indicates a group of using KM 2760 alone, ● indicates a group of using G-CSF alone, and □ indicates a group of combined use respectively. A bar indicates a standard deviation.

The chronological change in averages value of the tumor volume in each group is shown in FIG. 6. As shown in FIG. 6, antitumor effect was low in groups B and C compared to untreated group A, whereas an outstanding antitumor effect was observed in group D.

T/C values on the final day of evaluation are shown in Table 5. The antitumor effect (T/C value) in each group was evaluated by calculation using the following formula 3 for comparison between the average value of the tumor volume in group A and the average values of the tumor volume in each group on the final evaluation day (Day 14).

(T/C value)=(average value of tumor volume in each group on Day 14)/average value of tumor volume in group A on Day 14). (Formula 3)

In comparison with a theoretical value of T/C when simply adding the pharmaceutical effects of both KM 2760 and G-CSF, namely, a value obtained by multiplying T/C values of the groups of administering the respective agents alone, actual T/C value of the combined administration group (D in the table) exhibited the lower value (0.10) than 0.30, the theoretical value.

TABLE 5

| | Group | | | |
|---|---|---|---|---|
| A | B | C | D | Theoretical Value (B × C) |
| T/C value 1.0 | 0.48 | 0.63 | 0.10 | 0.30 |

From the foregoing, it has been clarified that the administration of KM 2760 and G-CSF in combination has the higher antitumor effect than the administration of KM 2760 or G-CSF alone, and exhibits the synergistic effect.

Example 7

Antitumor Effect Provided by Administrating an Anti-CCR4 Human Chimeric Antibody KM 2760 and IFN-α in Combination CCR4/EL4 cells were suspended in RPMI 1640 medium (manufactured by Gibco BRL) at a concentration of 5× cells/mL, and 100 µl of the suspension was grafted into the tail vein of C57BL/6 mice (CLEA Japan Inc., male, 8 weeks old). Further, mice were grouped into A to D, and each of the agents A to D were administered to the mice. Incidentally, the day on which the tumor was grafted was defined as Day 0.

A. Negative control group: No administration

B. Group of administering IFN-α alone: $5 \times 10^4$ units of IFN-α (Universal type I interferon, manufactured by PBL Biomedical Laboratories) was intravenously administered per mouse once a day for 5 days from Day 1 to Day 5.

C. Group of administering KM 2760 alone: 0.5 µg of KM2760 was intravenously administered per mouse once a day on Day 1 and Day 5.

D. Group of administering KM2760 and IFN-α in combination: 0.5 µg of KM 2760 was intravenously administered per mouse once a day on Day 1 and Day 5, and $5 \times 10^4$ units of IFN-α was intravenously administered per mouse once a day for 5 days from Day 1 to Day 5.

The experiment was conducted with group A consisting of 7 mice and groups B, C and D each consisting of 6 mice. KM 2760 was diluted with a citrate buffer solution (10 mM citric acid, 150 mM sodium chloride, pH 6) and IFN-α was diluted PBS containing 0.1% bovine serum albumin respectively. 100 µL of each of the diluents was administered. The weight of all mice was measured on Day 14. After etherization and exsanguination, mice were brought to euthanasia by dislocation of the cervical spine. The liver was extracted, and the weight of the liver was then measured. A ratio of the liver weight to the weight of each individual (hereinafter referred to as a weight ration of a liver) was calculated by percentage.

The antitumor effect was evaluated by comparing the liver weight ratio (average value of six mice) of untreated healthy mice measured simultaneously and the liver weight ratio of each group increased by metastasis of tumor cells.

Figure 7:
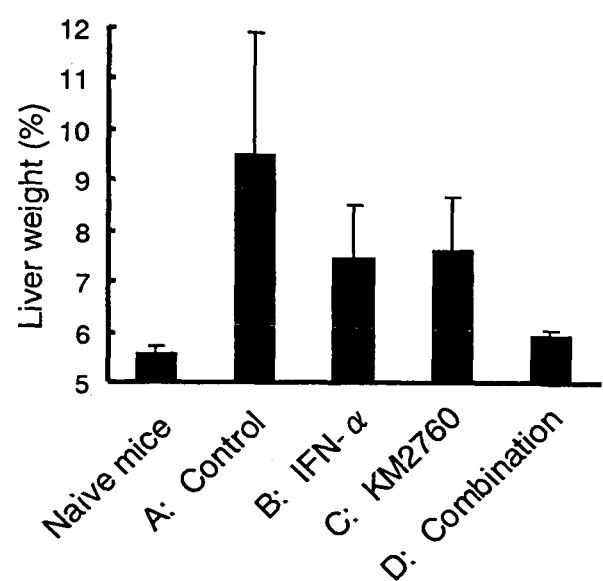
FIG. 7 shows an effect provided by combined use of an anti-CCR4 antibody and IFN-α against CCR4/EL4 cells grafted in C57BL/6 mouse. The ordinate shows a weight ratio of a liver. A bar indicates a standard deviation.

The liver weight ratio of each group is shown in FIG. 7. As shown in FIG. 7, antitumor effect was low in groups B and C compared to untreated group A, whereas an outstanding antitumor effect was observed in group D.

Further, the residual amount of tumor cells in the liver in each group was calculated as a T/C value using the following formula.

T/C=(average values of a weight ration of a liver of each group–average value of a weight ration of a liver of an untreated mouse) (average value of a weight ration of a liver of a negative control group–average value of a weight ration of a liver of an untreated mouse) (Formula 4)

The resulting T/C values are shown in Table 6. In comparison with a theoretical value of T/C when simply adding the pharmaceutical effects of both KM 2760 and IFN-α, namely, a value obtained by multiplying T/C values of the groups of administering the respective agents alone, actual T/C value of the combined administration group (D in the table) exhibited the lower value (0.088) than 0.25, the theoretical value.

TABLE 6

| | Group | | | | |
|---|---|---|---|---|---|
| | A | B | C | D | Theoretical Value (B × C) |
| T/C value | 1.0 | 0.48 | 0.52 | 0.088 | 0.25 |

From the foregoing, it has been clarified that the administration of KM 2760 and IFN-α in combination has the higher antitumor effect than the administration of KM 2760 or IFN-α alone, and exhibits the synergistic effect.

Example 8

Antitumor Effect Provided by Administrating an Anti-CCR4 Human Chimeric Antibody KM 2760 and M-CSF in Combination CCR4/EL4 cells (WO 01/64754) were suspended in RPMI 1640 medium (manufactured by Gibco BRL) at a concentration of $1 \times 10^5$ cells/mL, and 200 µL of the suspension was grafted into the peritoneal cavity of C57BL/6 mice (CLEA Japan Inc., male, 8 weeks old). After, mice was grouped into A to D, and each of the agents A to D was administered to each mouse. The day on which the tumor was grafted was defined as Day 0.

A. Negative control group: No administration

B. Group of administering M-CSF alone: 100 µg of M-CSF (Leucoprol, manufactured by Kyowa Hakko Kogyo Co., Ltd.) was intraperitoneally administered per mouse twice a day from Day-3 to Day-1 and once a day on Day 0, seven times in total.

C. Group of administering KM 2760 alone: 50 µg of KM2760 was intraperitoneally administered per mouse once a day on Day 0.

D. Group of administering KM 2760 and M-CSF in combination: 50 µg of KM 2760 was intraperitoneally administered per mouse once a day on Day 0, and 100 µg was intraperitoneally administered per mouse twice a day from Day-3 to Day-1 and once a day on Day 1, seven times in total.

The experiment was conducted with groups each consisting of 8 mice. Regarding the agents, KM 2760 was diluted with a citrate buffer (10 mM citric acid, 150 mM sodium chloride, pH 6), and M-CSF was diluted with a physiological saline solution (Otsuka Seiyaku) respectively. 100 µL of each of the diluents was administered. The antitumor effect was evaluated by a ratio of average values of the number of survival days of mice in each group to an average value of the number of survival days of mice in the negative control group (hereinafter referred to as a life prolongation ratio). The number of survival days of each mouse and the life prolongation ratio of each group are shown in Table 7.

As shown in Table 7, In comparison with untreated Group A, no antitumor effect was exhibited in group B, and antitumor effect was low in group C, whereas an outstanding antitumor effect was observed in group D. In comparison with a theoretical value of the life prolongation ratio when simply adding the pharmaceutical effects of both KM 2760 and M-CSF, namely, a value obtained by multiplying the life prolongation ratios of the groups of administering the respective agents alone, the actual life prolongation ratio of the combined administration group (D in the table) exhibited the higher value (>1.49) than 1.16, the theoretical value. Incidentally, one mouse in group D was still alive even after an observation period (Day 50).

From the foregoing, it has been clarified that the administration of KM 2760 and M-CSF in combination has the higher antitumor effect than the administration of KM 2760 or M-CSF alone, and exhibits the synergistic effect.

INDUSTRIAL APPLICABILITY

A medicament comprising a combination of a recombinant antibody which specifically binds to human CC chemokine receptor 4 (CCR4) or an antibody fragment thereof and at least one agent is provided.

SEQ ID No. 13—Description of an artificial sequence: Antibody heavy chain variable region amino acid sequence SEQ ID No. 14—Description of an artificial sequence: Antibody heavy chain variable region amino acid sequence SEQ ID No. 15—Description of an artificial sequence: Antibody light chain variable region amino acid sequence SEQ ID No. 16—Description of an artificial sequence: Antibody heavy chain variable region amino acid sequence SEQ ID No. 17—Description of an artificial sequence: Antibody heavy chain variable region amino acid sequence SEQ ID No. 18—Description of an artificial sequence: Antibody light chain variable region amino acid sequence

TABLE 7

| Group | Number of survival days | | | | | | | | Average number of survival days | Life prolongation ratio |
|---|---|---|---|---|---|---|---|---|---|---|
| A | 17 | 18 | 18 | 19 | 19 | 20 | 20 | 22 | 19.3 | 1.00 |
| B | 17 | 17 | 18 | 18 | 18 | 19 | 19 | 22 | 18.8 | 0.974 |
| C | 19 | 21 | 21 | 21 | 22 | 24 | 26 | 27 | 22.9 | 1.19 |
| D | 25 | 25 | 25 | 26 | 26 | 26 | 27 | >50 | >28.8 | >1.49 (theoretical value 1.16) |

The invention claimed is:

1. A method for treating a CCR4-expressing tumor in a patient, comprising administering to said patient a recombinant antibody or antigen-binding fragment thereof which specifically binds to human CC chemokine receptor 4 (CCR4), and at least one agent selected from the group consisting of G-CSF, M-CSF, interferon-α, IL 15, vincristine, cyclophosphamide, etoposide and methotrexate, wherein said agent is not conjugated to said antibody or antigen-binding fragment.

2. The method according to claim 1, wherein said CCR4-expressing tumor is a hematopoietic organ tumor.

3. The method according to claim 1, wherein said recombinant antibody or antigen-binding fragment thereof specifically binds to an extracellular region of CCR4, and does not specifically bind to human platelets.

4. The method according to claim 3, wherein said recombinant antibody or antigen-binding fragment thereof which specifically binds to the extracellular region of CCR4 does not have an activity of inhibiting binding of thymus and activation-regulated chemokine (TARC) or macrophage-derived chemokine (MDC) as a CCR4 ligand to CCR4.

5. The method according to claim 4, wherein said extracellular region is an extracellular region selected from the group consisting of positions 1 to 39, 98 to 112, 176 to 206 and 271 to 284 of the amino acid sequence as set forth in SEQ ID NO: 1.

6. The method according to claim 4, wherein said extracellular region is an epitope consisting of positions 2 to 29 of the amino acid sequence as set forth in SEQ ID NO: 1.

7. The method according to claim 4, wherein said extracellular region is an epitope consisting of positions 13 to 29 of the amino acid sequence as set forth in SEQ ID NO: 1.

8. The method according to claim 4, wherein said extracellular region is an epitope consisting of positions 13 to 25 of the amino acid sequence as set forth in SEQ ID NO: 1.

9. The method according to claim 8, wherein said recombinant antibody or antigen-binding fragment thereof which specifically binds to the extracellular region of CCR4 has a binding activity to a polypeptide comprising amino acids 13 to 25 of SEQ ID NO: 1, in which at least one of tyrosine residues 16, 19, 20 and 22 is sulfated, which is lower than a binding activity to a peptide comprising amino acids 13 to 25 of SEQ ID NO: 1.

10. The method according to claim 9, wherein said recombinant antibody or antigen-binding fragment thereof which specifically binds to the extracellular region of CCR4 specifically reacts with an epitope specifically bound by a monoclonal antibody produced by hybridoma KM 2160 (FERM BP-10090).

11. The method according to claim 10, wherein said recombinant antibody is a human chimeric antibody or a human CDR-grafted antibody.

12. The method according to claim 11, wherein said human chimeric antibody comprises complementarity determining regions (CDRs) of a heavy chain (H chain) variable region (V region) and a light chain (L chain) V region of a monoclonal antibody which specifically binds to CCR4.

13. The method according to claim 12, wherein said human chimeric antibody comprises CDR1, CDR2 and CDR3 domains of a heavy chain (H chain) variable region (V region) comprising the amino acid sequences as set forth in SEQ ID NOs: 5, 6 and 7, respectively, and CDR1, CDR2 and CDR3 domains of a light chain (L chain) variable region (V region) comprising the amino acid sequences as set forth in SEQ ID NOs: 8, 9 and 10, respectively.

14. The method according to claim 13, wherein said human chimeric antibody comprises a heavy chain (H chain) variable region (V region) comprising the amino acid sequence as set forth in SEQ ID NO: 11, and a light chain (L chain) V region of an antibody molecule comprising the amino acid sequence as set forth in SEQ ID NO: 12.

15. The method according to claim 11, wherein said human CDR-grafted antibody comprises complementarity determining regions (CDRs) of a heavy chain (H chain) variable region (V region) and a light chain (L chain) V region of a monoclonal antibody which specifically binds to CCR4.

16. The method according to claim 15, wherein said human CDR-grafted antibody comprises CDR1, CDR2 and CDR3 domains of a heavy chain (H chain) variable region (V region) comprising the amino acid sequences as set forth in SEQ ID NOs: 5, 6 and 7, respectively, and CDR1, CDR2 and CDR3 domains of a light chain (L chain) variable region (V region) comprising the amino acid sequences as set forth in SEQ ID NOs: 8, 9 and 10, respectively.

17. The method according to claim 16, wherein the human CDR-grafted antibody comprises a heavy chain (H chain) variable region (V region) comprising the amino acid sequence as set forth in SEQ ID NO: 16 or 17, and a light chain (L chain) V region of an antibody molecule comprising the amino acid sequence as set forth in SEQ ID NO: 18.

* * * * *

SEQUENCE LISTING

<160> NUMBER OF SEQ ID NOS: 18

<210> SEQ ID NO 1
<211> LENGTH: 360
<212> TYPE: PRT
<213> ORGANISM: Homo sapiens

<400> SEQUENCE: 1

Met Asn Pro Thr Asp Ile Ala Asp Thr Thr Leu Asp Glu Ser Ile Tyr
 1               5                  10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
        35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360

<210> SEQ ID NO 2
<211> LENGTH: 28
<212> TYPE: PRT
<213> ORGANISM: Homo sapiens

<400> SEQUENCE: 2

Asn Pro Thr Asp Ile Ala Asp Thr Thr Leu Asp Glu Ser Ile Tyr Ser
1               5                   10                  15

Asn Tyr Tyr Leu Tyr Glu Ser Ile Pro Lys Pro Cys
            20                  25

<210> SEQ ID NO 3
<211> LENGTH: 18
<212> TYPE: PRT
<213> ORGANISM: Homo sapiens

<400> SEQUENCE: 3

Asp Glu Ser Ile Tyr Ser Asn Tyr Tyr Leu Tyr Glu Ser Ile Pro Lys
1               5                   10                  15

Pro Cys

<210> SEQ ID NO 4
<211> LENGTH: 15
<212> TYPE: PRT
<213> ORGANISM: Homo sapiens

<400> SEQUENCE: 4

Asp Glu Ser Ile Tyr Ser Asn Tyr Tyr Leu Tyr Glu Ser Ile Pro
1               5                   10                  15

<210> SEQ ID NO 5
<211> LENGTH: 5
<212> TYPE: PRT
<213> ORGANISM: Mus musculus

<400> SEQUENCE: 5

Asn Tyr Gly Met Ser
1               5

<210> SEQ ID NO 6
<211> LENGTH: 17
<212> TYPE: PRT
<213> ORGANISM: Mus musculus

<400> SEQUENCE: 6

Thr Ile Ser Ser Ala Ser Thr Tyr Ser Tyr Tyr Pro Asp Ser Val Lys
1               5                   10                  15

Gly

<210> SEQ ID NO 7
<211> LENGTH: 10
<212> TYPE: PRT
<213> ORGANISM: Mus musculus

<400> SEQUENCE: 7

His Ser Asp Gly Asn Phe Ala Phe Gly Tyr
1               5                   10

<210> SEQ ID NO 8
<211> LENGTH: 16
<212> TYPE: PRT
<213> ORGANISM: Mus musculus

-continued

<400> SEQUENCE: 8

Arg Ser Ser Arg Asn Ile Val His Ile Asn Gly Asp Thr Tyr Leu Glu
 1               5                  10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
 1               5

<210> SEQ ID NO 10
<211> LENGTH: 9
<212> TYPE: PRT
<213> ORGANISM: Mus musculus

<400> SEQUENCE: 10

Phe Gln Gly Ser Leu Leu Phe Trp Thr
 1               5

<210> SEQ ID NO 11
<211> LENGTH: 138
<212> TYPE: PRT
<213> ORGANISM: Mus musculus

<400> SEQUENCE: 11

Met Asn Leu Gly Leu Ser Leu Ile Phe Leu Ala Leu Ile Leu Lys Gly
 1               5                  10                  15

Val Gln Cys Glu Val Gln Leu Val Glu Ser Gly Gly Asp Leu Met Lys
             20                  25                  30

Pro Gly Gly Ser Leu Lys Ile Ser Cys Ala Ala Ser Gly Phe Ile Phe
         35                  40                  45

Ser Asn Tyr Gly Met Ser Trp Val Arg Gln Thr Pro Asp Met Arg Leu
     50                  55                  60

Glu Trp Val Ala Thr Ile Ser Ser Ala Ser Thr Tyr Ser Tyr Tyr Pro
 65                  70                  75                  80

Asp Ser Val Lys Gly Arg Phe Thr Ile Ser Arg Asp Asn Ala Glu Asn
                 85                  90                  95

Ser Leu Tyr Leu Gln Met Asn Ser Leu Arg Ser Glu Asp Thr Gly Ile
            100                 105                 110

Tyr Tyr Cys Gly Arg His Ser Asp Gly Asn Phe Ala Phe Gly Tyr Trp
        115                 120                 125

Gly Arg Gly Thr Leu Val Thr Val Ser Ala
    130                 135

<210> SEQ ID NO 12
<211> LENGTH: 132
<212> TYPE: PRT
<213> ORGANISM: Mus musculus

<400> SEQUENCE: 12

Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
             20                  25                  30

Ser Leu Gly Asp Gln Ala Ser Ile Ser Cys Arg Ser Ser Arg Asn Ile
         35                  40                  45

Val His Ile Asn Gly Asp Thr Tyr Leu Glu Trp Tyr Leu Gln Arg Pro

```
                50                  55                  60
Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
                100                 105                 110

Phe Gln Gly Ser Leu Leu Pro Trp Thr Phe Gly Gly Gly Thr Arg Leu
                115                 120                 125

Glu Ile Arg Arg
            130

<210> SEQ ID NO 13
<211> LENGTH: 119
<212> TYPE: PRT
<213> ORGANISM: Artificial Sequence
<220> FEATURE:
<223> OTHER INFORMATION: Synthetic peptide

<400> SEQUENCE: 13

Glu Val Gln Leu Val Glu Ser Gly Gly Asp Leu Val Gln Pro Gly Arg
  1               5                  10                  15

Ser Leu Arg Leu Ser Cys Ala Ala Ser Gly Phe Ile Phe Ser Asn Tyr
                 20                  25                  30

Gly Met Ser Trp Val Arg Gln Ala Pro Gly Lys Gly Leu Glu Trp Val
             35                  40                  45

Ala Thr Ile Ser Ser Ala Ser Thr Tyr Ser Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Ala Arg His Ser Asp Gly Asn Phe Ala Phe Gly Tyr Trp Gly Gln Gly
                100                 105                 110

Thr Leu Val Thr Val Ser Ser
            115

<210> SEQ ID NO 14
<211> LENGTH: 119
<212> TYPE: PRT
<213> ORGANISM: Artificial Sequence
<220> FEATURE:
<223> OTHER INFORMATION: Synthetic peptide

<400> SEQUENCE: 14

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Gly Met Ser Trp Val Arg Gln Ala Pro Gly Lys Gly Leu Glu Trp Val
             35                  40                  45

Ser Thr Ile Ser Ser Ala Ser Thr Tyr Ser Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asp Gly Asn Phe Ala Phe Gly Tyr Trp Gly Gln Gly
```

Thr Leu Val Thr Val Ser Ser
        115

<210> SEQ ID NO 15
<211> LENGTH: 112
<212> TYPE: PRT
<213> ORGANISM: Artificial Sequence
<220> FEATURE:
<223> OTHER INFORMATION: Synthetic peptide

<400> SEQUENCE: 15

Asp Ile Val Met Thr Gln Ser Pro Leu Ser Leu Pro Val Thr Pro Gly
 1               5                  10                  15

Glu Pro Ala Ser Ile Ser Cys Arg Ser Ser Arg Asn Ile Val His Ile
            20                  25                  30

Asn Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Leu Pro Trp Thr Phe Gly Gln Gly Thr Lys Val Glu Ile Lys
            100                 105                 110

<210> SEQ ID NO 16
<211> LENGTH: 119
<212> TYPE: PRT
<213> ORGANISM: Artificial Sequence
<220> FEATURE:
<223> OTHER INFORMATION: Synthetic peptide

<400> SEQUENCE: 16

Glu Val Gln Leu Val Glu Ser Gly Gly Asp Leu Val Gln Pro Gly Arg
 1               5                  10                  15

Ser Leu Arg Leu Ser Cys Ala Ala Ser Gly Phe Ile Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Ser Ala Ser Thr Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Gly Arg His Ser Asp Gly Asn Phe Ala Phe Gly Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Synthetic peptide

<400> SEQUENCE: 17

```
Glu Val Gln Leu Val Glu Ser Gly Gly Asp Leu Val Gln Pro Gly Arg
  1               5                  10                  15

Ser Leu Arg Leu Ser Cys Ala Ala Ser Gly Phe Ile Phe Ser Asn Tyr
             20                  25                  30

Gly Met Ser Trp Val Arg Gln Ala Pro Asp Lys Arg Leu Glu Trp Val
         35                  40                  45

Ala Thr Ile Ser Ser Ala Ser Thr Tyr Ser Tyr Tyr Pro Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
             85                  90                  95

Ala Arg His Ser Asp Gly Asn Phe Ala Phe Gly Tyr Trp Gly Gln Gly
            100                 105                 110

Thr Leu Val Thr Val Ser Ser
            115

<210> SEQ ID NO 18
<211> LENGTH: 112
<212> TYPE: PRT
<213> ORGANISM: Artificial Sequence
<220> FEATURE:
<223> OTHER INFORMATION: Synthetic peptide

<400> SEQUENCE: 18

Asp Val Leu Met Thr Gln Ser Pro Leu Ser Leu Pro Val Thr Pro Gly
  1               5                  10                  15

Glu Pro Ala Ser Ile Ser Cys Arg Ser Ser Arg Asn Ile Val His Ile
             20                  25                  30

Asn Gly Asp Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
             85                  90                  95

Ser Leu Leu Pro Trp Thr Phe Gly Gln Gly Thr Lys Val Glu Ile Lys
            100                 105                 110
```